United States Patent
De Miguel Giraldo et al.

(10) Patent No.: US 9,557,302 B2
(45) Date of Patent: Jan. 31, 2017

(54) ULTRASOUND INSPECTION SYSTEM AND ULTRASONIC QUALITY CONTROL METHOD

(71) Applicant: Airbus Operations S.L., Getafe (Madrid) (ES)

(72) Inventors: Carlos De Miguel Giraldo, Getafe (ES); Gildas Lambert, Madrid (ES); Oscar Martinez, Madrid (ES); Luis Elvira, Madrid (ES); David Romero, Madrid (ES); Luis Gomez Ullate, Madrid (ES); Francisco Montero, Madrid (ES)

(73) Assignee: Airbus Operations S.L., Getafe (ES)

( * ) Notice: Subject to any disclaimer, the term of this patent is extended or adjusted under 35 U.S.C. 154(b) by 313 days.

(21) Appl. No.: 14/094,979

(22) Filed: Dec. 3, 2013

(65) Prior Publication Data

US 2014/0150557 A1 Jun. 5, 2014

(30) Foreign Application Priority Data

Dec. 3, 2012 (EP) ..................... 12382478

(51) Int. Cl.
*G01N 29/24* (2006.01)
*G01N 29/28* (2006.01)

(52) U.S. Cl.
CPC .......... *G01N 29/2493* (2013.01); *G01N 29/28* (2013.01); *G01N 2291/0231* (2013.01)

(58) Field of Classification Search
CPC ................ G01N 29/2493; G01N 29/28; G01N 2291/0231

(Continued)

(56) References Cited

U.S. PATENT DOCUMENTS 3,423,993 A * 1/1969 Lynnworth ........ G01N 29/2493
310/335
4,615,218 A * 10/1986 Pagano .............. G01N 29/2493
73/639

(Continued)

FOREIGN PATENT DOCUMENTS

EP 0001474 4/1979
EP 0305291 3/1989

(Continued)

OTHER PUBLICATIONS

An Ultrasonic wheel-array sensor and its application to aerospace structures, Brotherhood et al., Nov. 11, 2003.
European Search Report, May 3, 2013.

*Primary Examiner* — J M Saint Surin
(74) *Attorney, Agent, or Firm* — Greer, Burns & Crain Ltd.

(57) ABSTRACT

An ultrasound inspection roller provided with a wheel, a sensing system and a support for holding the sensing system inside the wheel, a wedge connected to the ultrasound sensing system at one end and provided with a curved profile at its other end facing the wheel, adapted to the curvilinear shape of the wheel, and a liquid of a density higher than $9.9*10^2$ kg/m$^{m3}$ placed inside the wheel such that the sensory system, the wheel and the wedge are acoustically coupled. The roller allows the early detection of problems during manufacturing of composites and the performance of corrective measures in real time, and assures a good coupling between the transducers and the material to be inspected in dry conditions.

11 Claims, 3 Drawing Sheets

(58) Field of Classification Search
USPC .......................................................... 73/635
See application file for complete search history.

(56) References Cited

U.S. PATENT DOCUMENTS

| | | | |
|---|---|---|---|
| 4,856,334 A | | 8/1989 | Shearer et al. |
| 5,708,191 A | * | 1/1998 | Greenwood ........... G01N 9/002 73/32 A |
| 5,814,731 A | * | 9/1998 | Alexander ........... G01N 29/225 73/624 |
| 6,082,181 A | * | 7/2000 | Greenwood ........... G01N 9/002 73/1.03 |
| 6,138,515 A | * | 10/2000 | Moufle ................ G01N 29/225 73/159 |
| 6,578,424 B1 | * | 6/2003 | Ziola .................... G01N 29/223 73/632 |
| 7,293,461 B1 | * | 11/2007 | Girndt .................... G01N 29/04 310/336 |
| 2004/0045358 A1 | | 3/2004 | Wagner et al. |
| 2012/0006132 A1 | * | 1/2012 | Faucher ............. G01N 27/9093 73/866.5 |

FOREIGN PATENT DOCUMENTS

| | | |
|---|---|---|
| EP | 1914544 | 4/2008 |
| GB | 1294404 | 10/1972 |
| WO | 2012131334 | 10/2012 |

* cited by examiner

ULTRASOUND INSPECTION SYSTEM AND ULTRASONIC QUALITY CONTROL METHOD

CROSS-REFERENCES TO RELATED APPLICATIONS

This application claims the benefit of the European patent application No. 12382478.1 filed on Dec. 3, 2012, the entire disclosures of which are incorporated herein by way of reference.

BACKGROUND OF THE INVENTION

The present invention is related to non-destructive inspection techniques to perform real time quality control of, in particular, but not limited to, fiber composite material manufacturing processes, out-of-autoclave curing processes and conventional processes such as autoclave. More in particular, the invention relates to a new technique based on an ultrasonic inspection system.

Most composite material parts manufactured today for the aeronautics industry are traditionally made according to autoclave curing processes. The main weaknesses of this technology include:

The inevitable heavy investment not only due to all the necessary equipment but also due to all the infrastructure associated with the autoclave process (space necessary, installation, tools, auxiliary materials, power consumption, maintenance, etc.);

The need of having a large enough autoclave to house the part to be manufactured, which clearly imposes a limitation on the design of the parts to be manufactured, reducing manufacturing flexibility; and The reduced process energy yield making the composite material parts manufactured according to this curing technology more expensive.

Among the options considered to overcome these drawbacks would be the use of alternative technologies for curing/reticulating the resin without the need of autoclave. Some of these technologies are electron beam curing, microwave curing, radiofrequency curing and induction curing. Each of these technologies has its advantages and drawbacks as well as its degree of maturity for different applications, and all of them have in common the elimination of the autoclave for the final curing of the part. Based on the need for a non-destructive inspection of the composite parts, and particularly parts manufactured according to the new processes, it is obvious that these new processes must be provided with a solution/an inspection technology which is capable of being adapted to the specific requirements of these processes, but which in turn maintain at least the capacities of the current systems for inspecting autoclave manufactured parts. The current non-destructive ultrasound testing techniques (NDT) perform quality control on the part once the part has been made and the material is completely cured.

NDTs have been used for decades to detect material and structural defects. The basic idea is simple: an electronic system excites an ultrasonic transducer generating a high frequency mechanical wave pulse which is introduced and propagates in the material to be inspected. When the ultrasonic pulse finds a heterogeneity inside the material, part of the incident energy is reflected in the form of an echo which returns to the transducer, where the vibrations are converted again into electrical signals. After amplification, the echoes indicate the presence of a defect, its position and size estimation.

These techniques have been greatly developed and have many applications in different industrial areas. They are particularly indispensable in the fields of aeronautics, energy generation, oil prospecting, rail transport and public works in which the verification of structure and part safety margins is an obligation and is performed with NDT techniques. Likewise, most manufacturing industries (metallurgy, automobile, machine-tool, etc.) use NDT techniques to assure the quality of their products.

The NDT systems have often been automated by associating them with robots that mechanically scan the parts to assure the structural integrity throughout their dimension.

Technology advancements over the past few years in the field of electronics and ultrasound transduction technologies have allowed performing inspections with a never before seen precision and speed. Currently the state of the art of the technology allows constructing very complex electronic systems from tens to several hundreds of channels, this is possible as a result of the mass integration of hardware processing functions provided by the technology.

The ultrasonic array-based technology facilitates arbitrary deflection and focusing of the ultrasonic beam in emission and reception without the need of moving or altering the transducer by means of an electronic control. The composition of the traces received allows constructing 2D and 3D images of the inside of the inspected materials. In fact, ultrasound has been used in medicine for almost three centuries with remarkable success.

Since the market appearance of the first successful system of NDT with arrays [FOCUS-TomoScan©, by Rd Tech, Canada] in 1996, this technology is being demanded by a growing number of users in different industrial sectors since the advantages it provides compensate its high cost.

One of the problems limiting the applicability of the inspection by means of ultrasounds on carbon fiber parts is the need of coupling the transducers to the materials. Due to the large acoustic impedance differences, great insertion losses occur between emission and reception if a suitable coupling means is not available. This is solved by, for instance, performing complete or partial immersions using water jets or micro-troughs, which is a cumbersome procedure, as in EP1914544A2, or need water films in contact with the material to be inspected to ultrasonically couple the transducer with such material.

SUMMARY OF THE INVENTION

The object of the present invention is to allow the early detection of problems during manufacturing of composites and the performance of corrective measures in real time, and assure a good coupling between the transducers and the material to be inspected in dry conditions. In particular, the method and inspection device of the invention guarantee:

Capacity of coupling to a moving surface with a processing speed which is capable of analyzing the component in real time as the carbon fiber—layers composing the composite lay-up are being added by the manufacturing tool;

Avoidance of materials/liquids which may contaminate or degrade the pre-preg material prior to the curing;

Suitable resolution for detecting material defects involving the mechanical property degradation of the component; and Dynamic range suitable for inspecting high attenuation materials such as composite materials.

For this purpose, the invention provides an ultrasound inspection roller provided with a wheel comprising, at least at its cover, an elastomer material, an ultrasound sensing system and a support for holding the sensing system inside the wheel, wherein a wedge is housed inside the roller connected to the ultrasound sensing system at one end and provided with a curved profile at its other end facing the wheel, the curved profile being adapted to the curvilinear shape of the wheel. Inside the wheel, a liquid of a density higher than $9.9*10^2$ kg/m3 enables the sensory system, the wheel and the wedge to be acoustically coupled. The material of the outer part (the elastomer) has preferably a hardness between 4 and 55 shore A hardness points, so that it is sufficiently deformed when applying a moderate pressure on the part to be inspected. The material of the wedge advantageously comprises rexolite and the liquid can be glycerol. Preferably, the thickness of the wheel (1) Er, thickness of a part to be inspected Ep, and the thickness of the wedge (4) Ec follow the relationships:

$$Er > Vr/Vp * Ep$$

$$Ec > 2 * Vc/Vp * Ep$$

wherein, Vr is the propagating speed of the wave in the wheel; Vp is the wave's propagating speed in the part, and Vc the speed in the wedge. The roller is specially designed for evaluating the quality of carbon fiber composite materials during the manufacturing thereof by means of out-of-autoclave curing processes.

The present method and system also facilitate the optimization of manufacturing parameters, as the effect of the variation of these parameters on the manufactured part can be determined instantly. The advantages of the invention are translated into:

Reduction in manufacturing time and cost of material as it allows early detection of the defect when it is really being generated and therefore stop the process before adding more value to the defective part;

Swift improvement of the manufacturing processes as it provides a system which allows instantly detecting the influence of each of the manufacturing parameters on the final material; and Increase in the reliability of the manufactured parts as a result of the more efficient manufacturing process optimization, as well as the reduction of interferences for inspection as a result of the geometry and final finishing of the part.

BRIEF DESCRIPTION OF THE DRAWINGS

To complete the description and in order to provide for a better understanding of the invention, a set of drawings is provided. Said drawings illustrate a preferred embodiment of the invention, which should not be interpreted as restricting the scope of the invention, but just as an example of how the invention can be embodied. The drawings comprise the following figures.

DETAILED DESCRIPTION OF THE PREFERRED EMBODIMENTS

Figure 1:
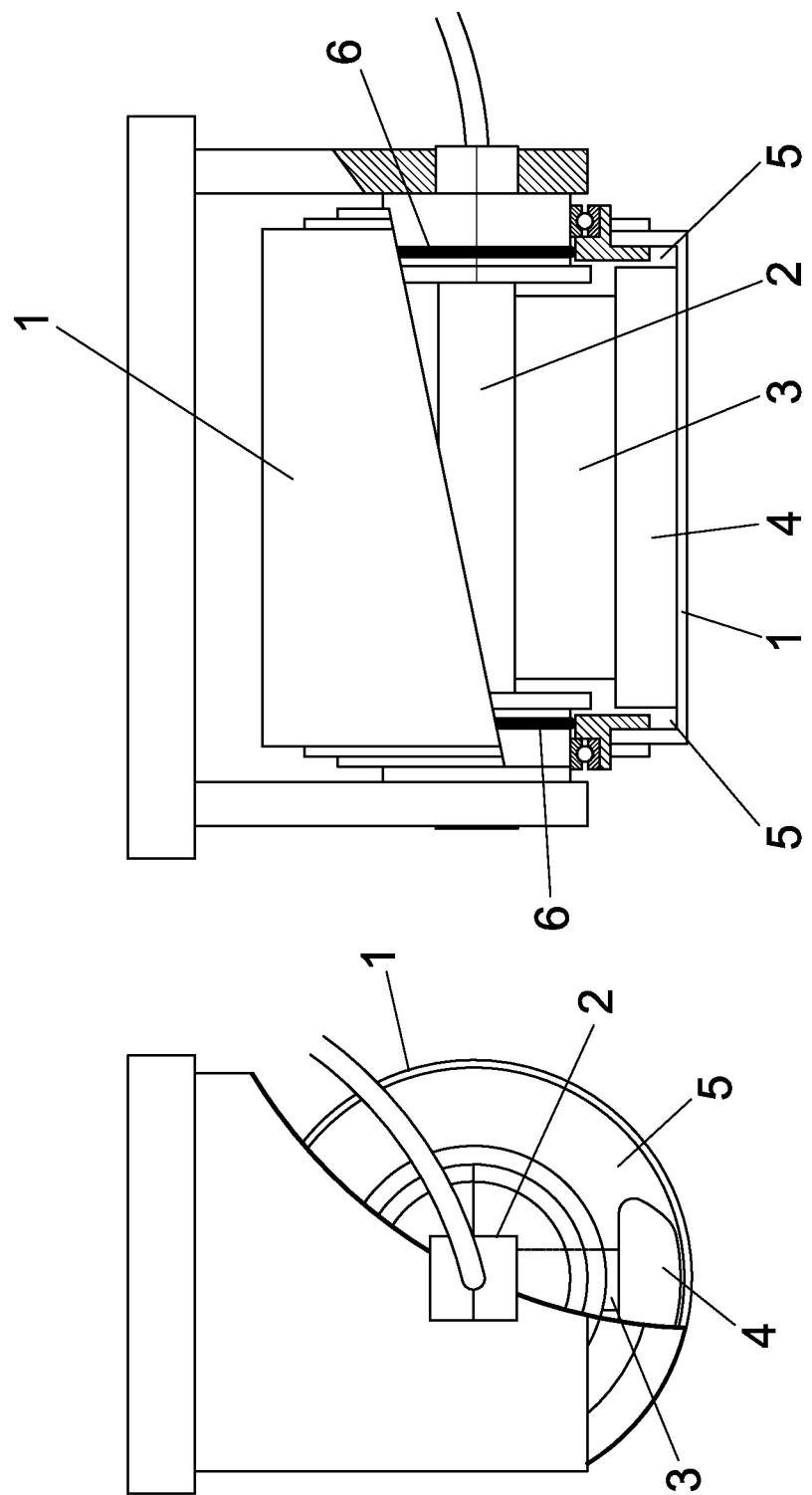
FIG. 1 shows the ultrasound inspection system according to the invention.
Figure 2:
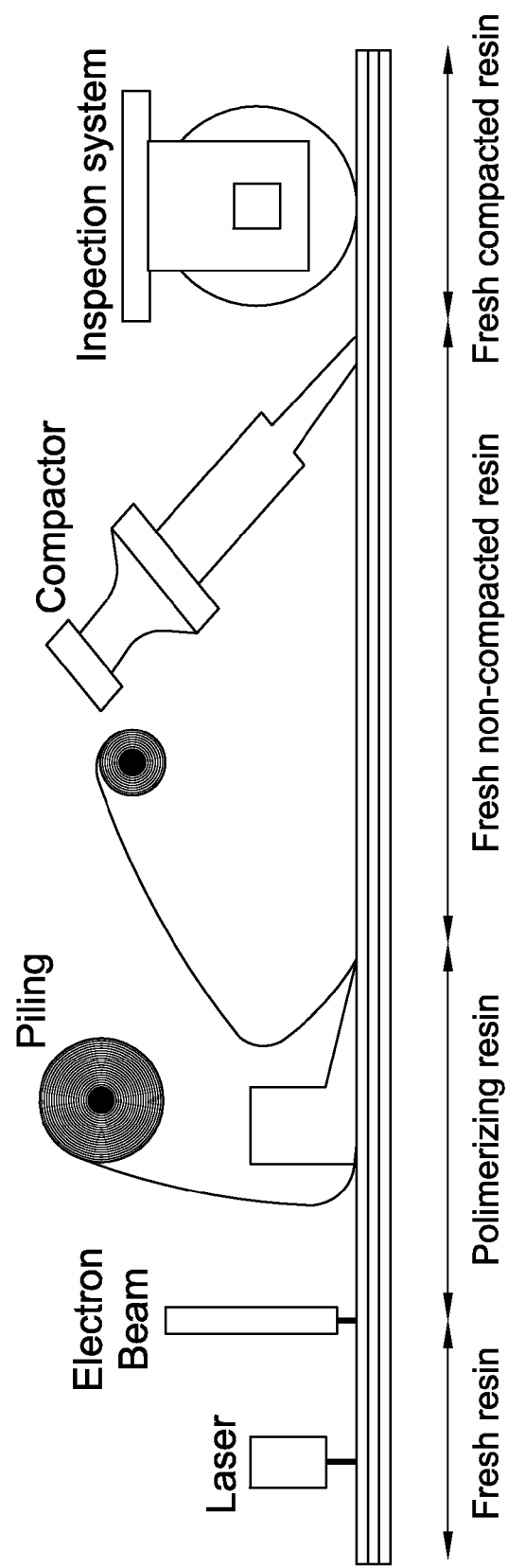
FIG. 2 shows a system for manufacturing CFRP laminate materials with out-of-autoclave curing incorporating the inspection system of the invention.
Figure 3:
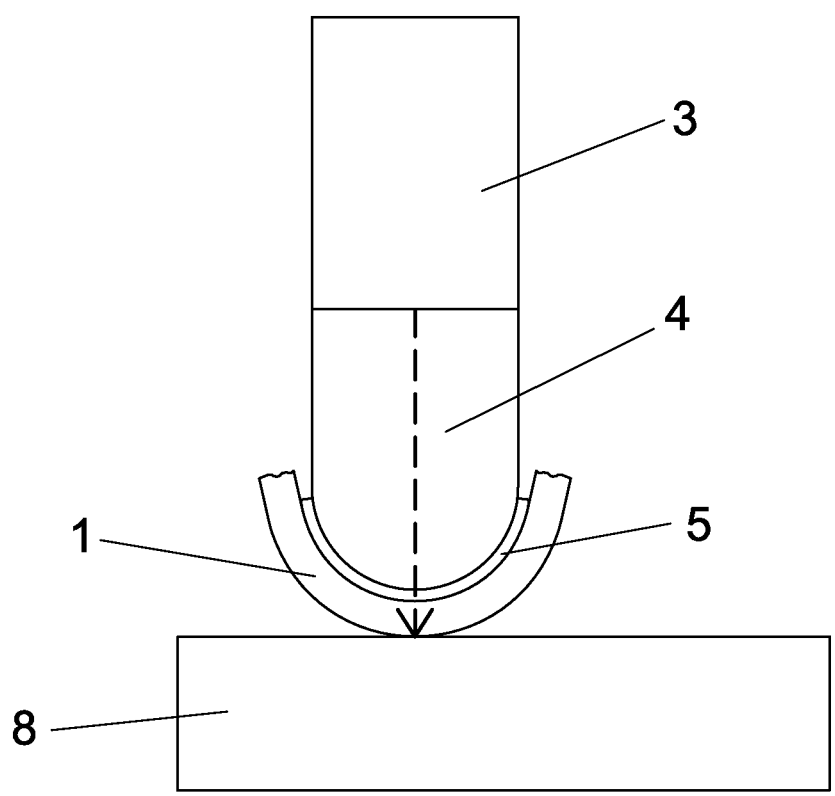
FIG. 3 shows a detail of the inspection roller of the present invention.

With reference to FIGS. 1 and 3, the invention developed is an inspection roller with an inspection wheel (1) which comprises, at least at its cover, an elastomer material filled with a high density liquid (5), thus allowing acoustic coupling with material to be inspected without the need of an additional liquid couplant in contact with the material to be analyzed. The wheel elastomer material (1) is preferably compatible with and innocuous to the fresh CFRP (pre-preg) to prevent contaminating same. The ultrasound sensing system (3) is attached to a support structure (2). This system rests on a wedge (4) with curved profile at its external face which is adapted to the curvilinear shape of the elastomer wheel (1). Lastly the system (3) is acoustically coupled to the wedge, and the latter to the wheel, by a high density liquid (5), with a density at least higher than water at room temperature, that is, higher than $9.9*10^2$ kg/m3 to reduce reflections through impedance decoupling. In a preferred embodiment, the liquid is glycerol. The system is leak-tight (6) to prevent said liquid losses. As it can be seen in FIG. 2, when the roller presses against the part to be inspected, an acoustic path among ultrasonic transducers—high density liquid—wedge with circular profile-high density liquid—deformed wheel—part to be inspected—is established. The presence of the high density liquid (5) therein also acts as a lubricant which allows the wheel (1) movement to be a sliding one. Furthermore, this liquid (5) does not have to be a pressurized liquid because it is the wedge (4) itself that exerts the necessary pressure, which significantly improves the mechanical coupling and favorably affects the resolution and dynamic range obtained with the system. The roller can be attached to springs at the side facing the part to be inspected, so that it is in tight contact with the part at all times when the latter is passed through the inspection line.

The sensory system formed by one or several transducers operates preferably by way of pulse-echo acquiring the echo wave resulting from the ultrasound propagation through the component under manufacturing during the process of rolling over the component. Operation in transmission mode is also possible, by placing receiving transducers at the opposite part of the piece being inspected. The signal is processed to obtain information of the presence of gaps in the material, delaminations, pores, lack of material, differences in the degree of curing of the material revealing information about the mechanical properties of the component. The frequency range of this sensory system is the common frequency range of the imaging systems ($10^5$-$10^7$ Hz), the limits being determined by the application conditions, below the dimensions of the defects to be detected and above the dispersive characteristics of the material. For application to inspection of carbon reinforced parts, this is preferably between 1 MHz and 10 MHz.

The signals acquired at a given time instant are associated with a specific position on the component and to a specific configuration thereof depending on the number of layers placed and on the curing state thereof. The correct labeling thereof allows evaluating the progress of the component curing and manufacturing process keeping a record which allows predicting the future appearance of defects and thus performing the necessary corrective actions to prevent component degradation.

The dimensions of the wheel, its diameter and its tread are advantageously determined by the component characteristics, the total thickness of the part to be examined and the width of the roll of the pre-preg material used in manufacturing, respectively. The maximum thickness of the component also determines the thickness of the wedge (4) which thickness must be the thickness which assures that the second echo of the ultrasonic wavefront with the external face of the wedge is located beyond the echo produced at the bottom of the part to be inspected. More specifically, and to prevent unwanted reflection problems during the signal analysis phase, the wave flight time through the wheel (Tr) must preferably be greater than the flight time in the part to be tested (Tp). Likewise, the ultrasound flight time through the wedge (Tc) will preferably be greater than the flight time in the wheel plus the ultrasound flight time of the part:

$$Tr>Tp$$

$$Tc>Tr+Tp$$

Therefore, $Tc>2Tp$

Based on these specifications, the ratio between thicknesses of the materials (Er, thickness of the wheel Ep, thickness of the part, and Ec, thickness of the wedge) can be obtained depending on the propagation speeds of the wave therein (Vr, speed in the roller; Vp, speed in the part, and Vc, speed in the wedge):

$$Er>Vr/Vp*Ep$$

$$Ec>2*Vc/Vp*Ep$$

With respect to the electronics, the voltage at which the transducer excitation circuit operates during emission must assure the ultrasound capacity of penetrating into the component and the reception step must allow changing reception gain with time to assure the detection of the bottom of the component. The transducers can be excited jointly or separately and the echo signals can be acquired on the same emitting transducer or on another. In any case it is necessary for the system to be able to associate each signal with the excitation and receiving transducer or the transducers for proper data processing. Data processing entails the generation of a B-scan type image which can be generated by beam forming techniques if the coordinated action of several elements is decided upon, and the corresponding C-scan and D-scan within one or several selected windows of interest according to the criterion of the evaluator. They must further be able to be contrasted with the record of prior material deposition runs.

In a particular embodiment, the ultrasound sensing system is chosen to work at a frequency of 5 MHz which is the "standard" frequency in ultrasound quality control processes in the aeronautics industry. This frequency provides a suitable commitment between resolution and penetration capacity for the materials used. The test frequency is undoubtedly an application-dependent variable which should be selected from a normal range of 1-10 MHz.

The multi-element ultrasound sensing system is organized in a piezoelectric array of 128 elements, although the number of elements can be adapted to the specific application. The array is coupled to a flat-convex rexolite part, a low attenuation polymer material. The flat section is attached to the array and the convex section will contact the roller through a thin layer of high density fluid couplant (in this case, glycerol). The contact between the plastic material and the roller allows pressing same on the CFRP part, improving the mechanical coupling.

In terms of the wheel, its external cover can be manufactured from different elastomer materials. One of the most important features for obtaining a good mechanical coupling is that the material of the wheel is sufficiently deformed when applying a moderate pressure on the part to be inspected (around 0.7 bar). For elastomers, this parameter is usually measured as the "shore" hardness of the material, values between 4 and 55, preferably 18 shore A hardness points (ISO 868) being desirable. To allow the rotation of the wheel about the axis containing the ultrasonic array, bearings were arranged coupled to parts that maintain the leak-tightness of the inside of the roller.

The ultrasound sensing system is secured to a metal structure which through a shaft, is secured to pneumatic actuators, which in turn are screwed to the mobile panel of the manufacturing machine. When the inspection process starts, the pneumatic actuators lower, contacting the wheel with the material to be inspected. At the same time, the rest of the elements of the manufacturing machine add the fabrics with resin, compacting and curing the material. Every time that each new fabric is placed, the pneumatic systems raise the roller, allowing the manufacturing system to move laterally to place the next fabric.

As the wheel is being moved over the material, the 128 transducers forming the ultrasound sensing system are being independently triggered in an alternate manner. The signals of preferably two consecutive transducers—to minimize grating lobes—are acquired in each trigger event including that of emission. When a specific number of them have been acquired, chosen by the system operator, these signals are processed as if it were an opening working in lineal scanning, forming a line within a B-scan image. The collection of signals made up of the 128 consecutive trigger events forms the B-scan image associated with the relative position of the wheel on the component. The different B-scans obtained in the deposition of each layer of material are grouped to be jointly processed in a window of interest determined by the operator. A C-scan type image and another D-scan type image which will show the possible presence of heterogeneities in the material are thus produced.

The method allows obtaining composite material information layer by layer during the process, not only with the capacity of inspecting the material but aiding the process optimization or even feeding back to the manufacturing system to attempt to correct defects, such as for instance lack of compaction, produced in the previous layers.

The inspection method also allows, in conjunction with the phase-array technology, varying the inspection parameters so that they can be optimized not only according to the thickness to be inspected, but even according to the defect to be detected (porosity, wrinkles, delaminations, lack of curing, etc.) These potentialities are obtained based on the features associated to phased array technology: dynamic focusing, variable aperture and steering capabilities.

With the implementation of receiving transducers on the other side of the part, which could be integrated in the manufacturing tool either adhered thereon or directly embedded therein it would be possible to work in transmission mode (TT) instead of pulse-echo (PE) ultrasound. The transmission technique broadens the dynamic range of thicknesses to be inspected since for that case the ultrasonic parameter to be controlled is not the eco reflection—affected by the intermediate interfaces and their secondary rebounds—but the transmitted signal.

As is apparent from the foregoing specification, the invention is susceptible of being embodied with various alterations and modifications which may differ particularly from those that have been described in the preceding specification and description. It should be understood that I wish to embody within the scope of the patent warranted hereon all such modifications as reasonably and properly come within the scope of my contribution to the art.

The invention claimed is:
1. An ultrasound inspection roller provided with a wheel comprising:

at least at its cover, a deformable material,
an ultrasound sensing system and
a support for holding the sensing system inside the wheel,
the ultrasound system further comprises a wedge connected to the ultrasound sensing system at one end and provided with a curved profile at its other end facing the wheel, configured to the curvilinear shape of the wheel, and
a liquid placed inside the wheel such that the sensory system, the wheel and the wedge are acoustically couple,
wherein the thickness of the wheel, Er, thickness of a part to be inspected, Ep, and the thickness of the wedge, Ec, follow the following relationships:

$$Er > Vr/Vp * Ep$$

$$Ec > 2 * Vc/Vp * Ep$$

wherein, Vr is the propagating speed of the wave in the wheel; Vp is the wave's propagating speed in the part, and Vc the speed in the wedge.

2. The ultrasound inspection roller according to claim 1 wherein the material is compatible with and innocuous to the fresh CFRP (pre-preg) to prevent contaminating the same.

3. The ultrasound inspection roller according to claim 1, wherein the material of the outer part is an elastomer material with a hardness between 4 and 55 shore A hardness points.

4. The ultrasound inspection roller according to claim 1, wherein the material of the wedge comprises rexolite.

5. The ultrasound inspection roller according to claim 1, wherein the liquid has a density higher than $9.9*10^2$ kg/m$^3$.

6. The ultrasound inspection roller according to claim 1, wherein the liquid is glycerol.

7. The ultrasound inspection roller according to claim 1, wherein the liquid is glycerol and has a density higher than $9.9*10^2$ kg/m$^3$.

8. A method for evaluating the quality of carbon fiber composite materials during the manufacturing thereof by means of out-of-autoclave curing processes, wherein it is performed by means of an ultrasonic inspection roller provided with a wheel comprising:
at least at its cover, a deformable material,
an ultrasound sensing system and
a support for holding the sensing system inside the wheel,
the ultrasound system further comprises a wedge connected to the ultrasound sensing system at one end and provided with a curved profile at its other end facing the wheel, configured to the curvilinear shape of the wheel, and
a liquid placed inside the wheel such that the sensory system, the wheel and the wedge are acoustically coupled.

9. The method according to claim 8, wherein the inspection of the material is performed layer by layer during the process.

10. The method according to claim 8, wherein the ultrasonic inspection operates by way of pulse-echo mode.

11. The method according to claim 8, wherein the ultrasonic inspection operates by way of transmission mode.

* * * * *